United States Patent [19]

Myers

[11] Patent Number: 4,885,347

[45] Date of Patent: Dec. 5, 1989

[54] POLYMER CONTAINING HINDERED AMINE LIGHT STABILIZING GROUPS AND PROCESS OF MAKING THE SAME

[75] Inventor: Terry N. Myers, Erie, N.Y.

[73] Assignee: Pennwalt Corporation, Philadelphia, Pa.

[21] Appl. No.: 295,870

[22] Filed: Jan. 11, 1989

Related U.S. Application Data

[60] Division of Ser. No. 87,473, Aug. 20, 1987, Pat. No. 4,872,823, which is a continuation-in-part of Ser. No. 831,393, Feb. 19, 1986, abandoned.

[51] Int. Cl.$^4$ .............................................. C08G 63/20
[52] U.S. Cl. ..................................... 525/447; 525/437
[58] Field of Search ................................. 525/447, 437

[56] References Cited

U.S. PATENT DOCUMENTS

| | | | |
|---|---|---|---|
| 4,042,773 | 8/1987 | Sheppard et al. | 546/208 |
| 4,045,427 | 8/1977 | Sheppard et al. | 260/192 |
| 4,129,586 | 12/1978 | Sheppard et al. | 560/108 |
| 4,336,183 | 6/1982 | Nakahara et al. | 524/95 |
| 4,499,273 | 2/1985 | Fontana et al. | 546/188 |

FOREIGN PATENT DOCUMENTS

56699 1/1982 European Pat. Off. ............ 546/242

OTHER PUBLICATIONS

Stanley W. Bukata et al., "Thermal Decomposition and Applications of n-butyl-4,4-Bis(tert-butylperoxy)valerate IEC Research and Development", vol. 3:262-264, Dec. 1964.

V. V. Zaitseva et al. "Investigation of the Kinetics of Diperoxide Decomposition," Zhurnal Organicheskoi Khimii vol. 4, No. 8, p. 1402-1406, Aug. 1968.

Primary Examiner—Joseph L. Schofer
Assistant Examiner—N. Sarofin
Attorney, Agent, or Firm—Panitch, Schwarze Jacobs & Nadel

[57] ABSTRACT

Compounds which contain peroxide linkages and the radical of a hindered amine light stabilizer group are provided. These compounds function as polymerization initiators which cause the hindered amine stabilizer to be chemically bound to the polymer.

10 Claims, No Drawings

POLYMER CONTAINING HINDERED AMINE LIGHT STABILIZING GROUPS AND PROCESS OF MAKING THE SAME

This application is a division of patent application Ser. No. 87,473, filed Aug. 20, 1987, now Pat. No. 4,822,823 which in turn is a continuation-in-part of copending application Ser. No. 831,393, filed Feb. 19, 1986, now abandoned.

BACKGROUND OF THE INVENTION

This invention relates to compounds which are free radical initiators and hindered amine light stabilizers.

It is well known that many ethylenically unsaturated monomers are polymerized using free radical initiators, i.e., those having peroxide groups. It is also well known that many of the polymers resulting from the polymerization of such monomers are subject to degradation by ultraviolet light, and, therefore, require the presence of an ultraviolet light stabilizer to extend the useful life of such polymers. Normally, such stabilizers are added to the polymer by methods such as milling or other methods of physical mixing. In more recent times, techniques of copolymerization have been used in which unsaturated derivatives of certain ultraviolet light stabilizing compounds have been copolymerized with vinyl monomers to form a light stabilized polymer. The method of physically mixing the stabilizer and the polymer has always been unsatisfactory because the resulting two-phase system is incompatible. The stabilizing compound inevitably migrates to the surface of the polymer and becomes separated from the polymer by evaporation, leaching, or erosion.

The copolymerization technique is more satisfactory than physically blending because it provides a chemically bound stabilizer which is not removed by physical processes. This method, however, has many inherent disadvantages because of the chemical equilibria involved in copolymerization reactions. The comonomer supplying the stabilizer component must have its reactivity balanced against that of the principle comonomer and the concentrations of these two comonomers adjusted to produce a product having the desired amount of stabilizer. The copolymerization technique also normally produces a product having more stabilizer incorporated into the polymer than is necessary, and this increases the cost of the final product markedly. Furthermore, many of the stabilizer comonomers have a tendency to homopolymerize rather than to copolymerize and thereby result in a product lacking homogeniety.

Hindered amine light stabilizers (hereinafter called HALS) are a class of compounds known to prevent and/or retard the degradation of polymers in which they are incorporated. Many patents on HALS additives and monomers are in the prior art (e.g., U.S. Pat. No. 4,336,183). The HALS compounds of the prior art suffer from the disadvantages stated above for UV stabilizers in general. The low molecular weight HALS have an added problem because they are water soluble which prevents their use because they are so readily leached from the polymer substrate upon exposure to moisture. Most patents issued on HALS disclose methods for making high molecular weight HALS which are less susceptible to leaching. This increase in molecular weight introduces problems of compatibility with the polymer to be stabilized and enhancement of the loss of the HALS additive by exudation. Also, increasing the molecular weight may produce adverse effect in cost or physical properties, since a greater amount of additive is necessary to assure the proper level of hindered amine functional group (which may represent only a small part of the high molecular weight additive).

A specific class of HALS peroxides known in the patent literature is perketals bearing a cyclic HALS moiety (European Pat. No. 56,699) and ammonium salts thereof (U.S. Pat. No. 4,499,273). These patents disclose the use of the perketals as crosslinkings and vulcanization agents. In these patents, the peroxygen groups are bonded directly to the piperidine ring of the HALS. The fragmentation of perketals during the initiation process assures that this combination of HALS and perketal initiator would not effectively bond the HALS to the polymer. (S. W. Bukata, L. L. Zabrocki, I&EC Product Research and Development, 1964(3), pp 261-264; V. V. Zaitseva, A. I. Yurzhenko, J. Org. Chem. USSR, 4(8), pp 1350-1353 (1968)). A perketal in which the peroxygen groups are not bonded directly to the piperidine ring would leave the piperidine stabilizer intact after the initiation process. Such remote perketal groups are envisioned as part of the current invention.

SUMMARY OF THE INVENTION

The present invention is directed to novel compounds which contain both a free radical initiator and a hindered amine light stabilizer.

A compound of this invention is a free radical initiator containing a hindered amine light stabilizer group having the formula:

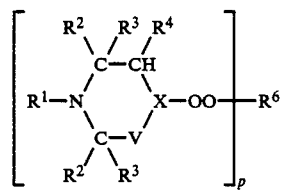

wherein:

p is 1 or 2.

$R^1$ is selected from hydrogen, substituted or unsubstituted aliphatic of 1-20 carbons, substituted or unsubstituted alicyclic of 5-12 carbons, substituted or unsubstituted araliphatic of 7-22 carbons, substituted or unsubstituted aliphatic acyl of 2-21 carbons, substituted or unsubstituted alicyclic acyl of 6-13 carbons, substituted or unsubstituted aryl acyl of 7-11 carbons, substituted or unsubstituted araliphatic acyl of 7-22 carbons, —C(=O)—N($R^4$)($R^5$), —C(=O)—O—$R^9$, and —(CH$_2$—CH($R^4$)—O)$_r$—$R^4$ where r is 2-50.

As used herein, the term "acyl" refers to a carboxylic acid group in which the OH of the carboxyl group is replaced by some other substituent Q, such that the acyl group would have the generalized formula QC(=O)—.

$R^2$ and $R^3$ may be the same of different and are independently selected from substituted or unsubstituted aliphatic of 1-20 carbons, substituted or unsubstituted aryl of 6-10 carbons, and substituted or unsubstituted araliphatic of 7-22 carbons. $R^2$ and $R^3$ can be taken together with the carbon to which they are attached to form a substituted or unsubstituted saturated alicyclic group of 4-12 carbons.

V is selected from —CH($R^5$)— and —C(=O)—.

R[4] and R[5] may be the same or different and are independently selected from hydrogen, substituted or unsubstituted aliphatic of 1-20 carbons, substituted or unsubstituted aryl of 6-10 carbons, and substituted or unsubstituted araliphatic of 7-22 carbons, substituted or unsubstituted alicyclic of 5-12 carbons which may optionally contain 1-3 heteroatoms selected from oxygen, sulfur, and nitrogen atoms in the ring, the nitrogen atom having a hydrogen atom or a methyl group bonded thereto, with the proviso that multiple heteroatoms must be separated from each other and from the portion of the compound to which the alicyclic group is bonded by at least one carbon atom.

When V is —CH(R[5])—, X is selected from

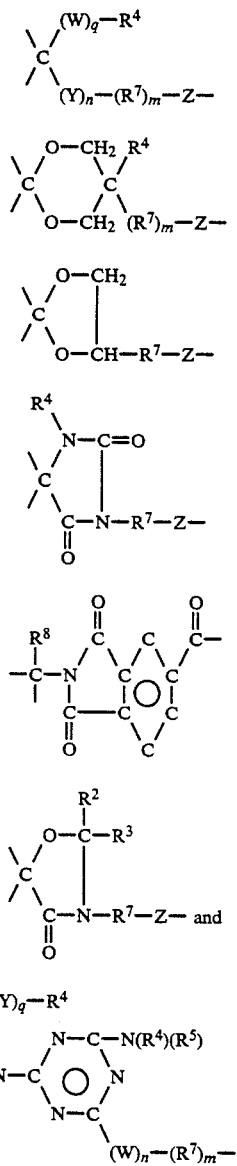

When V is —C(=O)—, X is

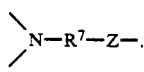

R[7] is selected from a substituted or unsubstituted aliphatic diradical of 1-20 carbons, substituted or unsubstituted aryl diradical of 6-10 carbons, substituted or unsubstituted alicyclic diradical of 5-12 carbons, and substituted or unsubstituted araliphatic diradical of 7-22 carbons. The diradical chain(s) may optionally contain 1-6 heteroatoms selected from oxygen, sulfur, and nitrogen atoms, the nitrogen atom having a hydrogen atom or a methyl group bonded thereto, with the proviso that multiple heteroatoms must be separated from each other and from the portions of the compound to which the diradical is bonded by at least one carbon atom.

R[8] is selected from hydrogen, substituted or unsubstituted aliphatic of 1-20 carbons, substituted or unsubstituted alicyclic of 5-12 carbons, substituted or unsubstituted aryl of 6-10 carbons, substituted or unsubstituted araliphatic of 7-22 carbons, —C(=O)—O—R[9], and —(CH$_2$—CH(R[4])—O)$_r$—R[5].

W is selected from —O—, —S—, and —N(R[5])—.

Y is selected from —Z—, —O—, —S—, —N(R[4])—, —S(=O)—, —O—S(=O)—, —O—S(=O)$_2$—, —NH—C(=O)—NH—, —O—C(=O)—O—, —C(=O)—O—, —O—C(=O)—C(=O)—O—, —O—C(=O)—C(=O)—N(R[4])—, —N(R[4])—C(=O)—C(=O)—O—, and —N(R[4])—C(=O)—C(=O)—N(R[4])—.

n, m and q are independently selected from 0 and 1 with the proviso that when m is 0, n must be 0.

Z is selected from —C(=O)—, —S(=O)$_2$—, —C(R[9])(R[10])—, —O—C(=O)—, —N(R[4])—C(=O)—, —O—C(=O)—C(=O)—, —N(R[4])—C(=O)—C(=O)—, —Si(R[4])(R[5])—, —Si(O—R[4])(O—R[5])—, and —P(O)(O—R[4])(O—R[5])—.

When p is 1, R[6] is selected from hydrogen, substituted or unsubstituted tertiary aliphatic of 4-24 carbons, substituted or unsubstituted tertiary alicyclic of 6-13 carbons, substituted or unsubstituted tertiary araliphatic of 9-24 carbons, substituted or unsubstituted aliphatic acyl of 2-21 carbons, substituted or unsubstituted aryl acyl of 7-11 carbons, substituted or unsubstituted araliphatic acyl of 7-22 carbons, —C(=O)—N(R[4])(R[5]), —C(=O)—O—R[9], —C(R[9])(R[10])—C(=O)—O—R[4], —S(=O)$_2$—R[4], and

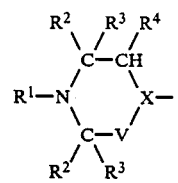

When p is 2, R[6] is selected from substituted or unsubstituted di-tertiary aliphatic of 6-27 carbons, substituted or unsubstituted di-tertiary alicyclic diradical of 7-14 carbons, substituted or unsubstituted di-tertiary araliphatic of 12-27 carbons, substituted or unsubstituted aliphatic diacyl of 3-21 carbons, substituted or unsubstituted alicyclic diacyl of 7-15 carbons, substituted or unsubstituted aryl diacyl of 8-12 carbons, or substituted or unsubstituted araliphatic diacyl of 9-24 carbons.

R[9] and R[10] are independently selected from substituted or unsubstituted aliphatic of 1-20 carbons, substituted or unsubstituted aryl of 6-10 carbons, substituted or unsubstituted araliphatic of 7-22 carbons, and substituted or unsubstituted alicyclic of 5-12 carbons which may optionally contain 1–3 heteroatoms selected from oxygen, sulfur, and nitrogen atoms in the ring, the nitrogen atom having a hydrogen atom or a methyl group bonded thereto, with the proviso that multiple heteroatoms must be separated from each other and from the portion of the compound to which the alicyclic group is bonded by at least one carbon atom. When both are present, $R^9$ and $R^{10}$ can be connected to each other by an alkylene diradical bridge containing 4–9 carbons, which may optionally contain 1–3 heteroatoms selected from oxygen, sulfur, and nitrogen atoms in the ring, the nitrogen atom having a hydrogen atom or a methyl group bonded thereto, with the provisos that multiple heteroatoms must be separated from each other and from the portions of the compound to which the diradical bridge is bonded by at least one carbon atom. When $R^6$ is t-alkyl, t-cycloalkyl, or t-aralkyl, $R^{10}$ may also be selected from —OO—$R^6$ and —O—$R^9$.

Optional substituents for $R^1$, $R^2$, $R^3$, $R^4$, $R^5$, $R^6$, $R^7$, $R^8$, $R^9$ and $R^{10}$ include one or more groups selected from halogen (—Cl, —Br), alkyl of 1–8 carbons, alkoxy of 1–8 carbons, —C≡N, —OH, epoxy

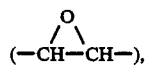

carboxy, alkyoxycarbonyl of 2–6 carbons, acyloxy of 1–4 carbons, acryloyl, acryloyloxy, methacryloyl, methacryloyloxy, hydroxymethyl, hydroxyethyl, alkylmercapto of 1–4 carbons and trialkoxysilyl of 3–12 carbons.

DETAILED DESCRIPTION OF THE INVENTION

The compound of this invention is a free radical initiator containing a hindered amine light stabilizer group having the formula:

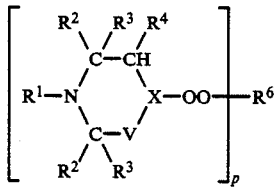

wherein:

p, $R^1$, $R^2$, $R^3$, $R^4$, V, X, and $R^6$ are as previously defined.

As a substituted or unsubstituted aliphatic of 1–20 carbons or substituted or unsubstituted araliphatic group of 7–22 carbons, $R^1$ is, for example, methyl, ethyl, n-propyl, isopropyl, allyl, propargyl, octadecyl, dodecyl, isododecyl, n-butyl, 2-hydroxyethyl, 2-hydroxypropyl, 2,3-epoxypropyl, dimethylaminoethyl, methoxycarbonylmethyl, butoxycarbonyl methyl, (benzyloxy)carbonylmethyl, benzyl, cinnamyl, 2-phenylethyl, cumyl, trimethylbenzyl, 4-octyloxybenzyl, naphthylmethyl, or (4-dodecylphenyl)methyl; preferably alkyl of 1–4 carbons, allyl, 2-hydroxyethyl, 2,3-epoxypropyl, 2-acetoxyethyl or benzyl.

As a substituted or unsubstituted aliphatic acyl of 2–20 carbons, substituted or unsubstituted alicyclic acyl of 7–16 carbons, substituted or unsubstituted aryl acyl of 7–11 carbons, or substituted or unsubstituted araliphatic acyl of 7–22 carbons, $R^1$ is, for example, formyl, acetyl, chloroacetyl, acryloyl, methacryloyl, propionyl, 2-methylpropionyl, crotonoyl, stearoyl, octadecanoyl, cyclohexylcarbonyl, 4-t-butylcyclohexylcarbonyl, 3-cyclohexenyl-1-carbonyl, cyclododecylcarbonyl, 4-octylcyclohexylcarbonyl, 2-methyl-4-octylcyclohexylcarbonyl, benzoyl, toluoyl, 4-chlorobenzoyl, isopropylbenzoyl, anisoyl, 3,5-di-t-butyl-4-hydroxybenzoyl, naphthoyl, 3-methyl-5-t-butyl-4-hydroxybenzoyl, 3,4,5-trimethoxybenzoyl, 4-4-dimethylaminobenzoyl, 3-(3,5-di-t-butyl-4-hydroxyphenyl)propionyl, cinnamoyl, or dihydrocinnamoyl; preferably alkanoyl of 2–5 carbons, cyclohexylcarbonyl, benzoyl or phenacyl.

As $(R^9)(R^{10})N$—C(=O)—, $R^1$ is, for example, methylcarbamoyl, n-butylcarbamoyl, dodecylcarbamoyl, dimethylcarbamoyl, diethylcarbamoyl, di-n-hexycarbamoyl, piperidin-1-ylcarbonyl, 2,2,6,6-tetramethyl-4-piperidinylcarbonyl, piperazine-1-carbonyl, morpholin-1-carbonyl, phenylaminocarbonyl, (4-butylphenyl)aminocarbonyl, alpha-naphthylaminocarbonyl, N-phenyl-N-hexylaminocarbonyl, N-(trimethylphenyl)-N-amylaminocarbonyl, diphenylaminocarbonyl, di-(4-methylphenyl)aminocarbonyl, or N-(4-benzylaminophenyl)-N-phenylaminocarbonyl.

As —C(=O)—O—$R^9$, $R^1$ is, for example, methoxycarbonyl, ethoxycarbonyl, or phenoxycarbonyl. As —(CH$_2$—CH($R^4$)—O)$_r$—$R^4$, $R^1$ is, for example, nonylphenoxypoly(ethoxy)ethyl, butoxypoly(propoxy)ethyl, or benzyloxypoly(tetramethyleneoxy)ethyl.

As substituted or unsubstituted aliphatic of 1–20 carbons, substituted or unsubstituted aryl of 6–10 carbons or substituted or unsubstituted araliphatic of 7–22 carbons, $R^2$ and $R^3$ are, for example, methyl, ethyl, n-propyl, isopropyl, octadecyl, dodecyl, isododecyl, n-butyl, benzyl, 2-phenylethyl, cumyl, trimethylbenzyl, 4-octyloxybenzyl, naphthylmethyl, (4-dodecylphenyl)methyl; preferably alkyl of 1–4 carbons or benzyl. When taken together with the carbon to which they are attached to form a saturated alicyclic group optionally containing heteroatoms, $R^2$ and $R^3$ are, for example, a cyclohexane ring, cyclooctane ring, or 2,2,6,6-tetramethylpiperidine ring.

As substituted or unsubstituted aliphatic of 1–20 carbons, substituted or unsubstituted aryl of 6–10 carbons or substituted or unsubstituted araliphatic of 7–22 carbons, $R^4$, $R^5$, $R^8$, $R^9$, and $R^{10}$ are, for example, methyl, ethyl, n-propyl, isopropyl, octadecyl, dodecyl, isododecyl, n-butyl, 2-methoxypropyl, phenyl 4-methylphenyl, 3,5-dimethoxyphenyl, benzyl, 2-phenylethyl, cumyl, trimethylbenzyl, 4-octyloxybenzyl, naphthylmethyl, (4-dodecylphenyl)methyl; preferably alkyl of 1–8 carbons, phenyl, or benzyl.

As a substituted or unsubstituted alicyclic of 5–12 carbons (optionally containing oxygen, sulfur, or nitrogen atoms in the ring with the proviso that multiple heteroatoms must be separated from each other by at least one carbon atom), $R^4$, $R^5$, $R^8$, $R^9$ and $R^{10}$ are, for example, cyclohexyl, trimethylcyclohexyl, cyclooctyl, cyclododecyl, or 2,2,6,6-tetramethyl-4-piperidinyl; preferably cycloalkyl of 5–7 carbons or 2,2,6,6-tetramethyl-4-piperidinyl.

As a substituted or unsubstituted aliphatic diradical of 1–20 carbons (optionally containing heteroatoms), substituted or unsubstituted aryl diradical of 6–10 carbons, substituted or unsubstituted alicyclic diradical of 5–12 carbons, or substituted or unsubstituted araliphatic diradical of 7–22 carbons, $R^7$ is, for example, methylene, ethane-1,2-diyl, hexane-1,6-diyl, 3-thiapentane-1,5-diyl, cyclohexane-1,4-dimethyl, 1,2-, 1,3-, or 1,4-phenylene, 1,2-, 1,3-, or 1,4-phenylene bis(methyl), or 3,6-dimethyl-3,6-diazaoctane-1,8-diyl; preferably alkylene of 1–10 carbons, arylene of 6–10 carbons, aralkylene of 8–16 carbons, or cycloalkylene of 4–8 carbons.

As a substituted or unsubstituted tertiary aliphatic of 4–24 carbons, substituted or unsubstituted tertiary alicyclic of 6–13 carbons, or substituted or unsubstituted tertiary araliphatic of 12–27 carbons, $R^6$ is, for example, t-butyl, t-amyl, t-octyl, 1,1-dimethyloctadecyl, 1,1-dimethyl-2-propynyl, 1,1-diethylpropyl, 1-methyl-1-ethylbutyl, 1,1-dimethyl-3-(acryloyloxy)butyl 1,1,3,3-tetramethylbutyl, 1-methyl-1-phenylethyl, 1-methyl-1-(4-t-butylphenyl)ethyl, 1-methyl-1-(4-isopropylphenyl)ethyl, or 1,1,4-trimethyl-4-hydroxypentyl; preferably substituted or unsubstituted t-alkyl of 4–10 carbons or substituted or unsubstituted t-aralkyl of 9–12 carbons.

As a substituted or unsubstituted aliphatic acyl of 2–20 carbons, substituted or unsubstituted aryl acyl of 7–11 carbons or substituted or unsubstituted araliphatic acyl of 8–22 carbons, $R^6$ is, for example, acetyl, chloroacetyl, acryloyl, methacryloyl, propionyl, 2-methylpropionyl, lauroyl, crotyl, stearoyl, octadecanoyl, cyclohexylcarbonyl, 4-t-butylcyclohexylcarbonyl, 3-cyclohexenyl-1-carbonyl, cyclododecylcarbonyl, 4-octylcyclohexylcarbonyl, 2-methyl-4-octylcyclohexylcarbonyl, benzoyl, toluoyl, 3-chlorobenzoyl, 3,5,5-trimethylhexanoyl, 2-ethylbutanoyl, 2-methylpentanoyl, 2,2-dimethylpropanoyl, 3-carboxyacryloyl, 2-carboxybenzoyl, 3-benzoylpropanoyl, isopropylbenzoyl, anisoyl, 3,5-di-t-butyl-4-hydroxybenzoyl, naphthoyl, 3-methyl-5-t-butyl-4-hydroxybenzoyl, 4-ethoxyphenylacetyl, 3,4,5-trimethoxybenzoyl, 3-(3,5-di-t-butyl-4-hydroxyphenyl)propanoyl, 3-carboxypropanoyl, 3-(trimethylsilyl)propanoyl, cinnamoyl, or dihydrocinnamoyl; preferably substituted or unsubstituted acyl of 2–10 carbons, or substituted or unsubstituted aroyl of 7–11 carbons.

As a substituted or unsubstituted di-tertiary aliphatic diradical of 7–27 carbons, substituted or unsubstituted di-tertiary alicyclic diradical of 7–14 carbons, or substituted or unsubstituted di-tertiary araliphatic diradical of 12–27 carbons, $R^6$ is, for example, 2,5-dimethylhexane-2,5-diyl, 2,5-dimethyl-3-hexyne-2,5-diyl, 1,4-, or 1,3-phenylenebis(1-methylethyl), 4,4'-biphenyldicarbonyl, 1,4-dimethylcyclohex-1,4-diyl, 1,4-phenylene bis(propanoyl), 1,4-, or 1,5-naphthalenebis(1-methylethyl); preferably, di-tertiary alkylene of 6–12 carbons, or ditertiary aralkylene of 12–15 carbons.

As a substituted or unsubstituted aliphatic diacyl of 3–21 carbons, substituted or unsubstituted alicyclic diacyl of 7–15 carbons, substituted or unsubstituted aryl diacyl of 8–12 carbons or substituted or unsubstituted araliphatic diacyl group of 9–24 carbons, $R^6$ is, for example, propane-1,3-dioyl, 1,4-butanedioyl, 2-butene-1,4-dioyl, alpha-(methoxycarbonyl)-1,4-butanedioyl, 1,6-hexanedioyl, 1,18-octadecanedioyl, phthaloyl, 7-[4'-(n-hexyl)-2'-cyclohexenyl]heptane-1,6'-dicarbonyl, isophthaloyl, or terephthaloyl; preferably substituted or unsubstituted alkanedioyl of 3–6 carbons, or aryl diacyl of 8–12 carbons.

Examples of compounds according to the present invention are as follows:

(1) O-[1,3-dimethyl-3-(t-butylperoxy)butyl] N-(2,2,6,6-tetramethyl-4-piperidinyl) carbamate
(2) OO-t-butyl N-methyl-N-(2,2,6,6-tetramethyl-4-piperidinyl) peroxycarbamate
(3) di[4-(2,3,6-trimethyl-2,6-diethyl-4-piperidinyloxy)-4-oxobutanoyl] peroxide
(4) 2,5-dimethylhexane-2,5-diyl bis[2-(1,2,2,6,6-pentamethyl-4-piperidinyloxy)peroxyacetate]
(5) cyclohexylsulfonyl 2-(2,2,6,6-tetramethyl-4-piperidinyloxy)acetyl peroxide
(6) OO,OO'-(2,5-dimethylhexane-2,5-diyl) bis[O-(2,2,6,6-tetramethyl-4-piperidinyl) monoperoxycarbonate]
(7) di{1,1-dimethyl-3-[N-methyl-N-(1-ethyl-2,2,6,6-tetramethyl-4-piperidinylamino)carbonyloxy]butyl} peroxide
(8) 1-methyl-1-phenylethyl 6-(1,2,2,6,6-pentamethyl-4-piperidinyloxy)-6-oxo-4-(thia)peroxyhexanoate
(9) 1,1,3,3-tetramethylbutyl 5-[7-aza-15-methyldispiro(5.1.5.3)hexadec-15-yloxy]-5-oxo-3-(oxa)peroxypentanoate
(10) O-[1,3-dimethyl-3-(1,1-dimethylpropylperoxy)butyl] N-benzyl-N-(2,2,6,6-tetramethyl-4-piperidinyl) carbamate
(11) OO-t-butyl O-{2-[1-(2,3-epoxypropyl)-2,2,6,6-tetramethyl-4-piperidinyloxycarbonyl]oxyethyl} monoperoxycarbonate
(12) OO-t-butyl O-(1,2,2,6,6-pentamethyl-4-piperidinyl) monoperoxyphthalate
(13) 1,1'-[1,4-phenylene-bis(1-methylethyl)] bis{2-[N-butyl-N-(2,2,6,6-tetramethyl-4-piperidinyl)amino]-peroxyacetate}
(14) 1-methylcyclohexyl 3-{N-[1-(2-propenyl)-2,2,6,6-tetraethyl-3,5-dimethyl-4-piperidinyl]-N-phenylamino}peroxypropanoate
(15) t-butyl 3-methyl-5-(1-benzyl-2,2,6,6-tetramethyl-4-piperidinyloxy)-5-oxo-3-(aza)peroxypentanoate
(16) OO-t-butyl O-[1-(n-octyl)-2,2,6,6-tetramethyl-4-piperidinyl] monoperoxyoxalate
(17) t-butyl 4-{N-methyl-N-[1-(2-chloroethyl)-2,2,6,6-tetramethyl-4-piperidinyl]aminosulfonyl}peroxybenzoate
(18) 4-(t-butylperoxycarbonyl)-N-(2,2,6,6-tetramethyl-4-piperidinyl)phthalimide
(19) t-butyl 2-[N-methyl-N-(2,2,6,6-tetramethyl-4-piperidinyl)amino]peroxyacetate
(20) OO-t-butyl O-[7,9-dimethyl-8,10-diethyl-8,10-dimethyl-9-aza-1,5-dioxaspiro(5.5)undecane-3-yl] monoperoxycarbonate
(21) t-butyl 3-carboxy-4-(2,2,6,6-tetramethyl-4-piperidinyl-oxycarbonyl)peroxybenzoate
(22) 1,2,2,6,6-pentamethyl-4-piperidinyl 3,3-di(t-butylperoxy)butanoate
(23) 1-methyl-3,3,5-trimethylcyclohexyl 2-[1-(ethoxycarbonylmethyl)-2,2,6,6-tetramethyl-4-piperidinyloxy]peroxyacetate
(24) 1,1,3,3-tetramethylbutyl 1,1,4-trimethyl-4-(2,2,6,6-tetramethyl-4-methoxy-4-piperidinyl-carbonyloxy)-2-pentynyl peroxide
(25) t-octyl 4-[di-(2,2,6,6-tetramethyl-4-piperidinyl)amino]-4-(oxo)peroxybutanoate
(26) 1-methyl-1-phenylethyl 3-[N-butyl-N-(2,2,6,6-tetramethyl-4-piperidinyl)amino]-3-(oxo)peroxypropanoate
(27) di-{9-[1-(phenoxycarbonyl)-2,2,6,6-tetramethyl-4-piperidinyloxy]-9-(oxo)nonanoyl}peroxide
(28) O-(2,2,6,6-tetramethyl-4-piperidinyl) OO-t-butyl phenylmonoperoxyphosphonate
(29) trimethylsilyl 3-[8-acetyl-1,3,8-triaza-7,7,9,9-tetramethyl-2,4-dioxo-dispiro(4.5)decan-3-yl]peroxypropanoate
(30) OO-(1-methyl-1-ethylpropyl) O-[8-aza-8-butyl-7,7,9,9-tetramethyl-1,4-dioxadispiro(4.5)decan-2-yl]methylmonoperoxycarbonate

(31) 1-methyl-1-{[4-(1-methyl-1-hydroxy)ethyl]phenyl}ethyl 3-[3,8-diaza-2,2,7,7,9,9-hexamethyl-1-oxa-4-oxodispiro(4.5)decan-3-yl]peroxypropanoate

(32) OO-(1,1,4-trimethyl-4-hydroxypentyl) O-(1-benzoyl-2,2,6,6-tetramethyl-4-piperidinyl) monoperoxycarbonate

(33) OO-t-butyl O-(1-morpholinylcarbonyl-2,2,6,6-tetramethyl-4-piperidinyl) monoperoxyoxalate

(34) t-amyl 3-(3,3,5,5-tetramethyl-2-oxopiperizinyl)-peroxypropanoate

(35) 1,1,3,3-tetramethylbutyl 3-[3,5-di(2,2,6,6-tetramethyl-4-piperidinylamino)-1,3,5-triazinylamino]peroxypropanoate

(36) 1,1-dimethyl-6-(methacryloxy)hexyl 4-(1-propanoyl-2,2,6,6-tetramethyl-4-piperidinylamino)-4-(oxo)-peroxybutanoate

(37) 2-phenoxyethyl 1-isobutanoyl-2,2,6,6-tetramethyl-4-piperidinyl peroxydicarbonate

(38) 1,1,3-trimethyl-3-(2,2,6,6-tetramethyl-4-piperidinyloxycarbonyloxy)butyl 3,5,5-trimethylperoxyhexanoate

(39) 1-methyl-1-{[4-(2,2,6,6-tetramethyl-4-piperidinyloxy)methyl]phenyl}ethyl 2-ethyl-peroxyhexanoate

(40) dodecanoyl 1-(2-hydroxyethyl)-2,2,6,6-tetramethyl-4-piperidinylcarbonyl peroxide The HALS-peroxide initiators of this invention can be prepared by a variety of techniques which are well-known in the art. Three preferred methods include: (a) reaction of HALS having pendant hydroxy, mercapto, or amino groups with peroxides containing acylating or alkylating functions, (b) reaction of HALS containing acylating or alkylating functions with peroxides containing reactive hydroxy, mercapto, amino, hydroperoxy, or carboxy groups, or (c) reaction of HALS containing ketone carbonyl with sufficient hydroperoxide to form the diperoxyketal.

Examples of acylating groups include acid chlorides, chloroformates, isocyanates, and esters.

Examples of alkylating groups are, for instance, reactive halogen or epoxide-containing compounds. The reaction to form the HALS-peroxide initiators can be done using any conditions which promote the reaction to create the desired product, and include the use of solvent (ethers, aromatic and nonaromatic hydrocarbons, chlorinated hydrocarbons, among others), acids and bases as may be needed to facilitate the formation. The application of heat may also be necessary for reaction to occur. However, the use of heat is possible only in so far as to complete the desired reaction without causing thermal decomposition of the peroxide group (the thermal or catalytic decomposition of this group is required in the later use of the invention to prepare polymer and cure unsaturated polyester resin).

Unsaturated polyester resins that can be cured by the composition of this invention usually include an unsaturated polyester and any polymerizable monomers. The unsaturated polyesters are, for instance, obtained by esterifying at least one ethylenically unsaturated di- or polycarboxylic acid, anhydride, or acid halide, such as maleic acid, fumaric acid, glutaconic acid, itaconic acid, mesaconic acid, citraconic acid, allylmalonic acid, allylsuccinic acid, tetrahydrophthalic acid and others with saturated or unsaturated di- or polyols, such as ethylene glycol, diethylene glycol, triethylene glycol, 1,2- and 1,3-propanediols, 1,2-, 1,3- and 1,4-butanediols, 2,2,-dimethyl-1,3-propanediol, 2-(hydroxymethyl)-2-methyl-1,3-propanediol, 2-buten-1,4-diol, 2-butyn-1,4-diol, 2,2,4-trimethyl-1,3-pentanediol, glycerol, pentaerythritol, mannitol and others. Mixtures of such polyacids and mixtures of such polyalcohols may also be used. The unsaturated di- or polycarboxylic acids may be partly replaced by saturated polycarboxylic acids, such as adipic acid, succinic acid, sebacic acid, and others or by aromatic polycarboxylic acids, such as phthalic acid, trimellitic acid, pyromellitic acid, isophthalic acid, and terephthalic acid. The acids used may be substituted by groups such as halogen. Examples of such suitable halogenated acids are, for instance, tetrachlorophthalic acid, 5,6-dicarboxy-1,2,3,4,7,7-hexachlorobicyclo(2.2.1)-heptene, and others.

The other component of the unsaturated polyester resin, the polymerizable monomer or monomers, are preferably ethylenically unsaturated monomers, such as styrene, chlorostyrene, vinyltoluene, divinylbenzene, alpha-methylstyrene, diallyl maleate, diallyl phthalate, dibutyl fumarate, acrylonitrile, triallyl phosphate, triallyl cyanurate, methyl acrylate, methyl methacrylate, N-butyl methacrylate, ethyl acrylate, and others or mixtures thereof, which are copolymerizable with said polyesters.

A preferred unsaturated polyester resin contains as the polyester component the esterification product of 1,2-propylene glycol (a polyalcohol), maleic anhydride (an anhydride of an unsaturated polycarboxylic acid) and phthalic anhydride (an anhydride of an aromatic dicarboxylic acid) and the monomer component, styrene.

Other unsaturated polyester resins that are useful in the practice of this invention are unsaturated vinyl ester resins, having of vinyl ester resin component and any polymerizable monomer components. The vinyl ester resin component can be made by reacting a chloroepoxide such as epichlorohydrin with proper amounts of a glycol such as bisphenol A (2,2-di-(4-hydroxyphenyl)-propane), in the presence of a base such as sodium hydroxide, to yield a condensation product having terminal epoxy groups derived from epichlorohydrin. Subsequent reaction of the condensation product with polymerizable unsaturated carboxylic acids in the presence or absence of acidic or basic catalysts, results in the formation of vinyl ester terminated resin component. Normally, styrene is added as the polymerizable monomer component to complete the preparation of the unsaturated vinyl ester resin.

Temperatures of about 20° to 200° C. and peroxide levels of about 0.05 to 5% or more by weight of curable unsaturated polyester resin are normally used in the curing process. The unsaturated polyester resins described above can be filled with various materials such as sulfur, glass fibers, carbon blacks, silicas, metal silicates, clays, metal carbonates, antioxidants, heat and light stabilizers, sensitizers, dyes, pigments, accelerators, metal oxides such as zinc oxide, blowing agents, etc.

The hindered amine-peroxide compound of the present invention is useful as a free radical initiator system for the polymerization or copolymerization of an ethylenically unsaturated monomer or mixtures thereof at suitable temperatures and pressures. The compound is useful not only in conventional isothermal polymerization processes but also in processes in which two or more increasing temperature steps are used or a continuous increase in temperature is used. Ethylenically unsaturated monomers include: olefins such as ethylene, propylene, styrene, alpha-methyl styrene, chlorostyrene, vinyl benzyl chloride, vinyltoluene, vinylpyridine, divinylbenzene; diolefins such as 1,3-butadiene, isoprene and chloroprene; vinyl esters such as vinyl acetate, vinyl propionate, vinyl laurate, vinyl benzoate or divinyl carbonate; unsaturated nitriles such as acrylonitrile and methacrylonitrile; acrylic acid, methacrylic acid and their esters and amides, such as methyl, ethyl, n-butyl and 2-ethylhexyl acrylates and methacrylates and acrylamide and methacrylamide; maleic anhydride; maleimide and N-substituted derivatives thereof such as N-phenylmaleimide; maleic and fumaric acids and their esters; vinyl halo and vinylidene halo compounds such as vinyl chloride, vinyl bromide, vinyl fluoride, vinylidene chloride and vinylidene fluoride; perhalo olefins such as tetrafluoroethylene, hexafluoropropylene and chlorotrifluoroethylene; vinyl ethers such as methyl vinyl ether, ethyl vinyl ether, n-butyl vinyl ether; allyl esters such as allyl acetate, allyl benzoate, diallyl phthalate, allyl ethyl carbonate, triallyl phosphate, triallyl cyanurate, diallyl fumarate, diallyl succinate, and diallyl carbonate; acrolein; methyl vinyl ketone; and mixtures thereof.

Temperatures of 30° to 250° C., preferably 40° to 200° C., and peroxide levels of 0.005 to 3%, preferably 0.01 to 1%, by weight, based on monomer, are normally used in the conventional polymerization or in the increasing temperature polymerization processes. Polymerization can be carried out in solution where solvents such as toluene may be used. Bulk, solution, suspension, or emulsion polymerization processes may be used. The HALS-peroxide composition of this invention may be used in these vinyl polymerization processes alone or together with other peroxide and azo initiators.

The hindered amine-peroxide composition of this invention is also useful for producing high impact polymers such as high impact polystyrene by initiating grafting of a monomer onto the backbone of elastomers (rubbers) such as polybutadienes, styrene-butadiene-styrene triblock copolymers, ethylene-propylene-diene terpolymers, etc. This composition is also useful with lower amounts of the rubber to produce high impact resistant polymers having impact resistance comparable to high impact polymers produced with larger amounts of rubber and conventional initiator systems. The above described vinyl polymerization conditions and initiator levels and up to 15% by weight of rubber (based on monoer) may be used for producing high impact polymers.

In the following examples, polymer molecular weight, when given, was determined by standardized gel permeation chromatography (GPC). The reported molecular weight data include Mn, Mw, and Mz (W. W. Yau, J. J. Kirkland, *Modern Size-Exclusion Liquid Chromatography*, John Wiley & Sons (New York), 1979, pp 4–14). Precision of the experimental determination is +5% for Mw. Mn and Mz are slightly less precise, +5 to 10%. The molecular weights were determined on a Waters Associates ALC-GPC 244 with Model 6000A solvent delivery system and Model R401 differential refractometer as detector. The four columns used were Waters Ultra-Styragel ™ with nominal pore sizes of $10^6$ Å, $10^5$ Å, $10^4$ Å and $10^3$ Å. The solvent was tetrahydrofuran, polymer samples for analysis were 0.2 to 0.3% by weight in the same solvent. Calibration for this system was done using TSK narrow molecular weight distribution polystyrene standards (range 500–$10^6$ MW).

EXAMPLE I

Preparation of OO-butyl O-1,2,2,6,6-pentamethyl-4-piperidinyl monoperoxycarbonate (C-I)

1. Preparation of 1,2,2,6,6-pentamethyl-4-(chlorocarbonyloxy)-piperidinium chloride Into a 2 liter round bottom flask equipped with an oil bath, reflux condenser, and nitrogen atmosphere sparger were charged 1,2,2,6,6-pentamethyl-4-piperidinol (51.2 g, 0.3 mole) and 1 liter of 2-butanone. Freshly distilled phosgene (35 ml, 0.45 mole) was evaporated into the reactor in a stream of nitrogen; a solid precipitate formed immediately. The resulting slurry was heated to reflux which initially was 53° C. but rose gradually over 25 minutes to 77° C. during which time the initially formed solid dissolved. After an additional 25 minutes of reflux at 77° C., the reaction mixture was cooled while being purged of excess phosgene and hydrogen chloride with a nitrogen stream. The ketone solvent was stripped from the product using an aspirator vacuum. The solid obtained was isolated and washed with 300 ml of 1,1,1-trichloroethane; then it was washed a second time with 200 ml of 1,1,1-trichloroethane. The resulting white crystalline solid was dried under high vacuum to give 76.5 g of the chloroformate hydrochloride having an assay of 99.7% (by analysis of hydrolyzable chloride: theoretical 26.24%, found 26.17%) and a corrected yield of 94.4%.

2. Preparation of C-I

Into a 1 liter flask equipped with an oil bath, thermometer, mechanical stirrer, reflux condenser, and nitrogen atmosphere sparger were combined poly-4-vinylpyridine (105.8 g, 0.9 equivalents) and 300 ml of toluene. The mixture was heated and 50 ml of toluene were collected (removed air and water from polymer). The mixture was cooled to ambient temperature and the reflux condenser was replaced with an addition funnel for the addition of t-butyl hydroperoxide (206.8 g, 2.2 mole), which was accompanied by a slight exotherm. After adjusting the temperature to 20° C. using an external ice/water bath, 1,2,3,6.6-pentamethyl-4-(chlorocarbonyloxy) piperidinium chloride (37.9 g, 0.14 mole) was added, again using an ice/water bath to control the slight exotherm and maintain reaction temperature 20°-25° C. The reaction mixture formed was allowed to stir at ambient temperature for four hours. The mixture was cooled and the poly-4-vinylpyridine was filtered from the solution with aid of a filter pad of anhydrous sodium sulfate. The polymer and sulfate were rinsed with 3 liters of pentane. The combined organic solutions were stripped of solvent using an aspirator vacuum and the residue was transferred to separatory funnel with 450 ml of pentane. The organic solution was washed four times with 150 ml of 5% aqueous sodium hydroxide then dried using anhydrous magnesium sulfate. The desiccant was filtered from the solution and the solution was treated with methylene chloride which had been saturated with hydrogen chloride. This caused the formation of a white crystalline solid. The solid was isolated and transferred to a separatory funnel with 200 ml of methyl t-butyl ether and 200 ml of 5% aqueous sodium hydroxide. The phases were separated and the organic solution was dried with anhydrous magnesium sulfate. The desiccant was filtered from the solution and the solvent was removed using aspirator vacuum. The monoperoxycarbonate was obtained as a slightly yellow liquid weighing 27.7 g. Analysis showed an assay of 93.7% and a corrected yield of 64.6%. Further structural proof was obtained from a proton NMR spectrum which agreed with the expected structure.

EXAMPLE II

Preparation of OO-t-amyl O-(1,2,2,6,6-pentamethyl-4-piperidinyl) monoperoxycarbonate (C-II)

Into a 125 ml flask equipped with a thermometer, mechanical stirrer, ice water bath, and nitrogen atmosphere sparger were combined aqueous potassium hydroxide (assay 45.3%, 21.8 g, 0.176 mole) and 10 g of water. The solution was cooled and t-amyl hydroperoxide (87% assay, 10.5 g, 0.088 mole) was added over a 5 minute period keeping the reaction temperature 5°-10° C. To the resulting mixture was then added 0.5 g of dimethylaminopyridine. The chloroformate hydrochloride prepared as in Example I (21.6 g, 0.08 mole) was added slowly over 10 minutes maintaining the reaction temperature 12°-18° C. After complete addition, the reaction was stirred at 15° C. for 10 minutes then warmed to 25° C. and stirred for 2 hours. The reaction mixture was transferred to a separatory funnel with 15 ml of water and 50 ml of hexane. The phases were agitated and then allowed to separate. The aqueous phase was removed and discarded. The organic phase was washed with four 50 ml portions of 10% sodium hydroxide and then dried with anhydrous sodium sulfate. The solvent was stripped using aspirator and high vacuum systems to give 22.2 g of clear slightly yellow liquid. Analysis showed an assay of 93.1% and a corrected yield of 86%. Residual t-amyl hydroperoxide was determined to be 0.3%. Upon heating in the differential scanning calorimeter at 4° C./minute, the onset of decomposition was observed at about 75° C. and the peak exotherm was about 125° C. The infrared spectrum showed the monoperoxycarbonate carbonyl at 1780 $cm^{-1}$.

EXAMPLE III

Preparation of 1,3-dimethyl-3-t-butylperoxybutyl 1,2,2,6,6-pentamethyl-4-piperidinyl carbonate (C-III)

1. Preparation of 1,2,2,6,6-pentamethyl-4-piperidinol, sodium salt

Into a dried 250 ml flask equipped with a reflux condenser and an oil bath were placed 7.45 g (0.0435 mole) of 1,2,2,6,6-pentamethyl-4-piperidinol, 1.35 g (0.0587 mole) of sodium and 100 ml of xylene. The mixture was heated to reflux for 16 hours and then cooled; and the unreacted sodium (0.225 g) was removed from the mixture. The alkoxide solution was used in the next step.

2. Preparation C-III

Into a dried 500 ml flask equipped with a magnetic stirbar, addition funnel, nitrogen atmosphere sparger, and a Dry Ice/acetone cooling bath were placed 11.6 g (0.435 mole) of 3-(t-butylperoxy)-1,3,-dimethylbutyl chloroformate and 30 ml of acetonitrile. The alkoxide prepared above was charged into the addition funnel with 20 ml of acetonitrile. The reaction mixture was cooled to less than 5° C. and the alkoxide was added dropwise over a 20 minute period forming an immediate precipitate and generating considerable foam. After the addition was completed, the reaction mixture was stirred for 1 hour at 0°-5° C. and then for 2.5 hours at ambient temperature. The reaction mixture was transferred to a separatory funnel with 100 ml of methyl t-butyl ether and extracted with three 50 ml portions of 5% sodium hydroxide and three 50 ml portions of water. The organic phase was dried with anhydrous magnesium sulfate and the solvent was stripped using aspirator vacuum to remove acetonitrile and leaving the xylene. A methylene chloride solution saturated with hydrogen chloride was added dropwise to the xylene solution until the solution was acidic to moist pH paper. The hydrochloride salt of C-III was precipitated by the addition of 500 ml of pentane. The salt was filtered and transferred to a separatory funnel containing 100 ml of methyl t-butyl ether and 100 ml of 5% aqueous sodium hydroxide. The aqueous phase was removed and the organic solution was washed once with 50 ml of 5% sodium hydroxide and once with 50 ml of water. The organic mixture was dried using anhydrous magnesium sulfate and then stripped of solvent using aspirator vacuum. The liquid residue was taken up in 50 ml of pentane which caused some unreacted piperidinol to precipitate. This was removed by filtration and the pentane solution was washed twice with very dilute aqueous acetic acid (1 drop conc. acetic acid/100 ml water) and once with 50 ml of 5% sodium hydroxide. The pentane solution was dried again with anhydrous magnesium sulfate and the solvent stripped using an aspirator vacuum. The desired peroxide was obtained as a slightly yellow liquid weighing 5.2 g. Liquid chromatographic analysis indicated that the product was essentially of one component. Assuming 100% assay, the correct yield was 30.8%. The NMR spectrum of the product confirmed the structure for C-III.

When 2,2,6,6-tetramethyl-4-aminopiperidine and a tertiary amine base was substituted for the piperidinyl alkoxide used in this preparation, reaction with 3-(t-butylperoxy)-1,3-dimethylbutylchloroformate produces O-(1,3-dimethyl-3-(t-butylperoxy)butyl) N-(2,2,6,6-tetramethyl-4-piperidinyl) carbamate.

EXAMPLE IV

Preparation of OO-t-butyl 0-(2,2,6,6,-tetramethyl-4-piperidinyl) monoperoxycarbonate (C-IV)

1. Preparation of 2,2,6,6-tetramethyl-4-(chlorocarbonyloxy)piperidinium chloride Into a 500 ml flask equipped with a magnetic stirbar, thermometer, gas inlet adapter, dual condensers (i.e., Dry Ice condenser atop a water cooled condenser), and oil bath were placed 28.2 g (0.145 mole) of 2,2,6,6-tetramethyl-4-piperidinol hydrochloride and 250 ml of 2-butanone. The mixture was heated to reflux and 8.0 ml (0.11 mole) of condensed phosgene was allowed to evaporate into the reaction mixture cooling the mass to 73°-75° C. This was followed by pipet addition of 11.5 g (0.145 mole) of pyridine which caused an exothermic reaction raising the temperature to 80° C. An additional 10 ml (0.14 mole) of phosgene were evaporated into the system. During this time the reaction mixture cleared of initially suspended solid and then formed a precipitate. After the addition of phosgene was completed, nitrogen was bubbled into the system for 40 minutes under continued reflux. The mixture was then allowed to cool gradually overnight and then was cooled further in an ice water bath. The very hygroscopic solid was collected by filtration. The liquid was reduced to 50 ml volume by distillation at atmospheric pressure, cooled to ambient, and diluted with 100 ml of tetrahydrofuran. In this manner, more solids were obtained and isolated by filtration. The combined solids were then freed from residual solvent under high vacuum. The product was a mixture of the tetramethylpiperidinium chloride compound and pyridinium hydrochloride. This mixture was used in the next step without further purification.

2. Preparation of C-IV

Into a 500 liter flask equipped with mangetic stirbar, thermometer, and Dry Ice/acetone cooling bath were placed 204.2 g of aqueous 15% potassium hydroxide (0.546 mole KOH). This was cooled to −5° to 0° C. and 51.9 g (0.52 mole) t-butyl hydroperoxide (assay 90.3%) were added by pipet maintaining the aforementioned temperature range, The solution was transferred to a separatory funnel, was extracted with 50 ml of hexane, was then returned to the reaction vessel, and was again cooled to −5° C. Tetrahydrofuran (45 ml) was added forming an upper layer. The salt mixture prepared in step 1 was added in small parts, using a cooling bath to maintain −5° C. The reaction mass thickened and 25 ml of methyl t-butyl ether were added to ease stirring. The reaction mixture was allowed to warm to ambient temperature and stirred for 3 hours. The mixture was transferred to a separatory funnel with 250 ml of methyl t-butyl ether and the phases were allowed to separate. The aqueous phase was removed and the organic phase was extracted with two 50 ml portions of 15% potassium hydroxide, two 50 ml portions of cold water, and 50 ml of buffered sulfite solution (prepared from water, acetic acid, sodium acetate and sodium sulfite). Before removal of the buffered sulfite wash, it was made basic by addition of 15% potassium hydroxide. A final wash with 50 ml of 5% sodium bicarbonate was preformed. The organic solution was stripped of solvent using an aspirator vacuum. The residue was mixed with 30 ml of water and the pyridine/water azeotrope was removed under high vacuum. The semi-solid aqueous residue was dissolved in 120 ml of methyl t-butyl ether and transferred to a separatory funnel. Solid sodium chloride was added to prepare a saturated aqueous phase which was separated. The organic phase was dried using anhydrous magnesium sulfate and the solvent stripped using aspirator and high vacuum systems. The yellow liquid residue solidified upon standing in the freezer. The solids were further high vacuum stripped for 4 hours, broken up with a mortar and pestle, then stripped again for 1.5 hours. The product was obtained as a white solid weighing 32.2 g and having a melting point of 52°-57° C. This product was identified as the 1:1 complex of the C-IV compound and t-butyl hydroperoxide.

Into a 300 ml flask equipped with a magnetic stirbar, thermometer, addition funnel and ice water cooling bath were placed 23.3 g (0.064 mole) of the complex prepared above and 50 ml of methyl t-butyl ether. The addition funnel was charged with 93.1 g of buffered sulfite solution and this solution was added dropwise to the complex mixture while maintaining the reaction temperature below 10° C. After addition was completed, the cooling bath was removed and the solution was allowed to stir at ambient temperature for 1.5 hours. To the reaction mixture was then added 24.4 g of aqueous 15% potassium hydroxide and 25 ml of methyl t-butyl ether. The reaction mass was transferred to a separatory funnel. The aqueous phase was separated and extracted once with 20 ml of methyl t-butyl ether. The combined organic solutions were dried with anhydrous magnesium sulfate and stripped of solvent using aspirator and high vacuum systems. The residue crystallized upon cooling. The solids were dissolved in pentane and chilled to precipitate 2,2,6,6-tetramethyl-4-piperidinol. This impurity was removed by filtration and the liquid filtrate stripped using aspirator and high vacuum systems to give the C-IV as a viscous yellow liquid weighing 12.4 g. Analysis showed an assay of 93.7% and a corrected yield of 29.2%.

EXAMPLE V

Preparation of OO-t-butyl O-(1-acetyl-2,2,6,6,-tetramethyl-4-piperidinyl)-monoperoxycarbonate (C-V)

Into a 50 ml flask equipped with a magnetic stirbar, nitrogen atmosphere and oil bath were placed C-IV (0.61 g, 0.002 mole), 25 ml of acetic anhydride and 0.04 g of dimethylaminopyridine. The reaction continued for about 90 hours at 40° C. and about 280 hours at ambient temperature (heat application during the day, standing at ambient overnight). The reaction mixture was transferred to a beaker containing ice and 75 ml of methyl t-butyl ether. The two-phase solution was stirred while sufficient 50% caustic was added to bring the pH to 14. The basic mixture was poured into a separatory funnel and the aqueous phase was discarded. The organic phase was washed twice with 30 ml portions of 5% sodium hydroxide and once with 50 ml of 5% sodium bicarbonate, then dried using anhydrous magnesium sulfate. The solvent was stripped using aspirator and high vacuum systems yielding 0.35 g of soft tan solid. The purity of C-V was determined using liquid chromatography and the structure was confirmed using proton NMR spectroscopy (singlet 1.4 ppm, 9H; multiplet 1.8 to 2.4 ppm with singlet 2.2 ppm, 7H; doublet 1.1 and 1.2 ppm, 6H; doublet 1.5 and 1.6 ppm, 6H, multiplet about 5.1 ppm; 1H).

EXAMPLE VI

Preparation of t-butyl 4-(1,2,2,6,6-pentamethyl-4-piperidinyloxy)-4-oxoperoxybutanoate (C-VI)

Into a 500 ml flask equipped with a magnetic stirbar, thermometer, addition funnel, and nitrogen atmosphere sparger were placed 7.6 g (0.044 mole) of 1,2,2,6,6-pentamethyl-4-piperidinol, 4.4 g (0.044 mole) of triethylamine, and 100 ml of pentane. The addition funnel was charged with 9.7 g (0.044 mole) of 4-t-butylperoxy-4-oxobutanoyl chloride, 50 ml of methyl t-butyl ether and 50 ml of pentane. The acid chloride was added dropwise to the reaction mixture at a rate maintaining the temperature of the reaction less than 27° C. (about 70 min. for complete addition). After this addition, the reaction mixture was allowed to stir at ambient temperature for 45 minutes. To the mixture 100 ml of 5% aqueous sodium hydroxide (chilled to 5° C.) was then added with rapid stirring. The mixture was transferred to a separatory funnel with 100 ml of methyl t-butyl ether and 100 ml of pentane. The funnel was shaken and allowed to separate; and the aqueous phase was drawn off. The organic phase was extracted with 100 ml of aqueous 5% sodium hydroxide (chilled to 5° C.), and twice with 100 ml portions of cold (5° C.) water. The organic solution was dried with anhydrous sodium sulfate and the solvent was stripped using aspirator and high vacuum systems. The residue was transferred to a flask with 30 ml of pentane and treated with 5.3 g of decolorizing carbon (occasional swirling for 90 minutes). The mixture was diluted with 200 ml of pentane, filtered free from carbon, and stripped of solvent using aspirator and high vacuum. The product was a yellow oil weighing 9.7 g. Analysis showed an assay of 96.1% and corrected yield of 62.2%.

EXAMPLE VII

Preparation of t-butyl 4-(2,2,6,6-tetramethyl-4-piperidinylamino)-4-(oxo)-peroxybutanoate (C-VII)

Into a 250 ml flask equipped with a magnetic stirrer, thermometer, condenser, addition funnel and calcium chloride drying tube were placed 2,2,6,6-tetramethyl-4-aminopiperidine (20.3 g, 0.13 mole) and 50 ml of methylene chloride. The addition funnel was charged with 4-t-butylperoxy-4-oxobutanoyl chloride (13.2 g, 0.06 mole) and 50 ml methylene chloride. The acid chloride was added dropwise at 20°-23° C. over a 20 minute period, causing a slight exotherm. The reaction mixture was warmed to 30° C. over 60 minutes and then stirred at 30° C. for another 30 minutes. The reaction mixture was poured into a jacketed reactor and washed at 20°-25° C. with eight 50 ml portions of water. The organic material was dried with anhydrous magnesium sulfate and the solvent stripped under reduced pressure to give 9.3 g of a light amber-straw liquid. Liquid chromatography of this product showed it to contain two components, one of which was 4-t-butylperoxy-4-oxobutanoic acid. Iodometric analysis indicated 5.65% active oxygen content which corresponds to a mixture of 22% perester-acid and 78% perester-amide (C-VII). The infrared spectrum (neat) showed three carbonyl absorptions at 1650, 1700 and 1770 $cm^{-1}$ (amide, acid and perester) and a broad absorption at 3300 $cm^{-1}$. Based on the 78% assay, the product was prepared in 37% corrected yield.

EXAMPLE VIII

Preparation of 1-(2-acetoxyethyl)-2,2,6,6-tetramethyl-4-piperidinyl 3-t-butylperoxy-1,3-dimethylbutyl carbonate (C-VIII)

1. Preparation of 1-(2-acetoxyethyl)-2,2,6,6-tetramethyl-4-piperidinol

Into a 250 ml flask equipped with a magnetic stirbar, thermometer, addition funnel and nitrogen atmosphere was placed 1-(2-hydroxyethyl)-2,2,6,6-tetramethyl-4-piperidinol (10.0 g, 0.499 mole) and 75 ml of methylene chloride. The resulting slurry was cooled to −20° C. and the addition funnel was charged with acetic anhydride (5.1 g, 0.496 mole) and 15 ml of methylene chloride. The anhydride was added dropwise to the diol slurry with no apparent reaction. The mixture was warmed to 15° C. at which temperature the solids began to dissolve. The mixture was stirred at ambient temperature for 2 hours. The mixture was poured into 80 ml of 10% sodium carbonate (aqueous) and stirred for 15 minutes at ambient temperature. The mixture was transferred to a separatory funnel and extracted with 100 ml of methyl t-butyl ether. The ether solution was dried with anhydrous magnesium sulfate and the solvent removed using aspirator and high vacuum systems. The product was a white solid melting at 56°-58° C. This material was used without further purification.

2. Preparation of C-VIII

Into a 250 ml flask equipped with a magnetic stirbar, thermometer, addition funnel and nitrogen atmosphere was placed the piperidinol prepared above (5.44 g, 0.211 mole), 30 ml of methylene chloride and pyridine (1.83 g, 0.0232 mole). The solution was cooled to 5° C. and the addition funnel was charged with 3-t-butylperoxy-1,3-dimethylbutyl chloroformate (5.78 g, 0.211 mole) in 20 ml of methylene chloride. The chloroformate solution was added dropwise to the piperidinol keeping the reaction temperature below 10° C. The resulting mixture was stirred for 1 hour at ambient temperature, then refluxed for 3 hours. The mixture was transferred to a separatory funnel with 100 ml of methyl t-butyl ether and washed with 40 ml of 10% sodium carbonate (aqueous) and then dried with anhydrous magnesium sulfate. The solvent was stripped using aspirator and high vacuum systems to yield an oil. This oil was taken up in 100 ml of pentane and washed with five 40 ml portions of cold water and 25 ml of 5% sodium bicarbonate. The organic solution was dried and stripped of solvent as before to yield 7.0 g of light yellow oil. By liquid chromatography, the oil was determined to be about 90% assay thus giving a corrected yield of 63.2%. The infrared spectrum showed the carbonate carbonyl at 1745 $cm^{-1}$. During heating in the differential scanning calorimeter at 20° C./minute, the onset of decomposition was observed at 150° C. and the peak exotherm at 197° C.

EXAMPLE IX

Preparation of 4-(t-amylperoxycarbonyl)-N-(2,2,6,6-tetramethyl-4-piperidinyl)phthalimide (C-IX)

1. Preparation of 4-carboxy-N-(2,2,6,6-tetramethyl-4-piperidinyl)phthalimide Into a 125 ml flask equipped with thermometer, magnetic stirbar and condenser were combined (in order) acetic acid (250 ml), trimellitic anhydride (10.3 g, 0.053 mole), potassium acetate (15.7 g, 0.16 mole), and 2,2,6,6-tetramethyl-4-piperidinylamine (25.1 g, 0.16 mole). The resulting mixture was heated to reflux. Most of the solids dissolved upon heating but were quickly replaced by a thick precipitate. The mixture was refluxed for 6 hours. The hot mixture was poured into a 1 liter beaker packed with ice. The solution was stirred until the ice melted and the solid was isolated by filtration. The solid was slurried with 200 ml of tetrahydrofuran and filtered again. The solid was dried on the filter funnel. The product was 12.4 g of white solid with melting point >225° C. Upon standing, the original filtrate formed more solids. These were isolated and combined with previously isolated product to give a total of 13.8 g of material (78.4% of theoretical).

2. Preparation of 4-(chlorocarbonyl)-N-(2,2,6,6-tetramethyl-4-piperidinyl)phthalimide, hydrochloride salt Into a 250 ml flask equipped with a magnetic stirbar and condenser were combined the acid chloride prepared above (8.8 g, 0.027 mole) and thionyl chloride (150 ml). The mixture was heated to reflux and refluxed for 1 hour (until cessation of gas evolution). The excess thionyl chloride was stripped using aspirator vacuum and the solid residue was isolated using methylene chloride. The solid was slurried with more methylene chloride and filtered a second time. The solid was dried briefly under high vacuum to give 10.3 g of product (100% of theoretical).

3. Preparation of C-IX

Into a 500 ml flask equipped with magnetic stirbar, thermometer and ice water bath were combined (in order) pyridine (100 ml), t-amyl hydroperoxide (14.4 g 0.13 mole, assay 97% by active oxygen) and the acid chloride prepared above (10.3 g, 0.027 mol). All the additions were done maintaining the reaction temperature at 15°-20° C. None of the additions was noticeably exothermic. The mixture was warmed to ambient temperature and stirred for 45 minutes. The excess pyridine was stripped at ambient temperature using a high vacuum system. The viscous yellow oil which remained was transferred to a separatory funnel with 250 ml of methyl t-butyl ether and 100 ml of 5% sodium hydroxide. The mixture was shaken and the aqueous phase removed. The ether solution was washed with two more 100 ml portions of 5% sodium hydroxide, and three 100 ml portions of water. The organic solution was dried with anhydrous magnesium sulfate, the desiccant was filtered and the solvent removed using aspirator and high vacuum systems. The solid residue was mixed with 100 ml tetrahydrofuran and 40 ml of buffered sulfite solution and stirred for 45 minutes. The mixture was transferred to a separatory funnel with 200 ml of methyl t-butyl ether and 100 ml of 5% sodium hydroxide. The mixture was shaken and the aqueous phase removed. The ether solution was washed with two 100 ml portions of water and 50 ml of saturated aqueous sodium chloride. The organic phase was dried with anhydrous magnesium sulfate. The desiccant was filtered and the solvent stripped using aspirator and high vacuum systems. The residue was mixed with water and the water/pyridine azeotrope was distilled under high vacuum. The aqueous mixture was transferred to a separatory funnel and the product extracted using methylene chloride. The methylene chloride extract was dried with anhydrous magnesium sulfate and the solvent stripped using aspirator and high vacuum systems. The yellow oil residue was mixed with a small amount of pentane which caused the product to crystallize. The product was isolated and dried on the funnel. The product purity was ascertained by active oxygen analysis which showed an assay of 92.2%. The melting range was 126°-130° C. The infrared spectrum further confirmed the product as the desired HALS-peroxide.

EXAMPLE X

Curing unsaturated polyester resin

The stabilizer initiators of the instant invention were used to prepare polyester with bound stabilizer groups. Gelation and cure characteristics were determined using Standard SPI Exotherm Procedure ("SPI Procedures for Running Exotherm Curves—Polyester Resin," published in the Preprint of the 16th Annual Conference—Reinforced Plastics Division, society of the Plastics Industry, Inc., February 1961). The results are shown in Table I.

TABLE I

| Initiator | Gel Time (min) | Cure Time (min) | Exotherm Max (°F.) | Barcol Hardness |
|---|---|---|---|---|
| C-I | 4.5 | 5.1 | 446 | 35–45 |
| C-III | 7.0 | 8.0 | 432 | 35–45 |
| C-IV | 4.8 | 5.5 | 433 | 35–45 |
| C-VI | 10.4 | 12.6 | 402 | 35–45 |
| t-butyl perbenzoate | 5.1 | 5.8 | 418 | 35–45 |
| di-t-butyl peroxide | 11.6 | 14.3 | 348 | 30–40 |
| di-cumyl peroxide | 6.5 | 7.8 | 397 | 35–45 |
| Lupersol 233-M090* | 6.0 | 6.7 | 430 | 35–45 |

Initiator concentration: $4.0 \times 10^{-3}$ molar
Resin:
E-4297-7 (a one component low profile isomolding resin marketed by Owens Corning Fiberglass)
Filler: 100 phr calcium carbonate
Cure Temperature: 260° F.
*Ethyl 3,3-di(t-butylperoxy)butyrate, 90% solution in paraffinic oil

EXAMPLE XI

Preparation of Acrylic Terpolymer

Methyl n-amyl ketone (300 g) was heated to 145° C. in a jacketed glass reactor equipped with a stirrer, thermometer, reflux condenser, and nitrogen gas sparging line. A mixture of 40 g of methyl methacrylate, 53 g of isobutyl methacrylate, 30 g of 2-hydroxyethyl methacrylate, and 3.7 g of HALS peroxide C-VI was prepared. A 100 g portion of this mixture was added uniformly at a rate of 25 g per hour to the refluxing solvent over 4 hours. After the monomer/initiator addition was completed, the polymerization was continued for one hour. The coatings resin was obtained in 74% monomer conversion and had the following molecular weight data by GPC:

$\overline{M}w = 11,000$
$\overline{M}n = 5,300$
$\overline{M}z = 18,000$
$\overline{M}w/\overline{M}n = 2.1$

EXAMPLE XII

Preparation and Accelerated Weathering of High Solids Coating Resin

1. Preparation of high solids coating resin Aromatic 100 (60 g, from Exxon) was heated to 129° C. in a jacketed glass reactor equipped with a stirrer, thermometer, reflux condenser, and nitrogen gas sparging line. A mixture of 30 g butyl acrylate, 20 g butyl methacrylate, 25 g 2-hydroxyethyl acrylate, 12 g methyl methacrylate, 10 g styrene and 3 g methacrylic acid, and peroxide as shown below was prepared. This mixture was added uniformly at a rate of 20 g per hour to the refluxing solvent over 5 hours. After the monomer/initiator addition was completed, the polymerization was continued for one hour. This procedure was repeated twice using initiators as follows:

| Resin | Initiator | gms. | Temperature (°C.) |
|---|---|---|---|
| A | HALS-peroxide C-II | 2.18 | 129 |
| B | Lupersol TAEC* | 1.89 | 129 |

The coatings resins obtained all had 60–62% nonvolatile material (NVM) and the following molecular weight data by GPC:

| Resin | Mn | Mw | Mz |
|-------|------|-------|-------|
| A | 5300 | 17000 | 45000 |
| B | 5200 | 13500 | 30000 |

By isolation of some of the resin from composition A and nitrogen analysis, the assay for hindered amine nitrogen was found to be 0.81%.

2. Preparation of coatings

Both resins prepared above were used to prepare stabilized clear single coatings drawn down on aluminum panels. The clear coat formulations were as follows:

| Component | Formulation A | Formulation B |
|-----------|---------------|---------------|
| Resin A | 38.4 g | |
| Resin B | | 38.0 g |
| Cymel 303* | 12.8 g | 12.6 g |
| Aromatic 100 | 23.5 g | 23.3 g |
| DBE Solvent* | 9.3 g | 9.2 g |
| methyl amyl ketone | 9.3 g | 9.2 g |
| n-butanol | 6.2 g | 6.2 g |
| Cycat 4040* | 0.5 g | 0.5 g |
| Tinuvin 440* | | 1.02 g |
| % hindered nitrogen | | |
| (total) | 0.0389 | 0.0328 |
| (polymer bound) | 0.0315 | 0.0000 |

*Cymel 303 is a modified melamine crosslinking agent commercially available from American Cyanamid; DBE solvent is a mixture of esters available from Dupont; Cycat 4040 is an aromatic sulfonic acid solution in isopropanol available from American Cyanamid; and Tinuvin 440 is a hindered amine light stabilizer available from Ciba-Geigy.

The coatings were baked onto the panels at 140° C. for 30 minutes.

3. Accelerated weather test

The panels prepared above were placed in a QUV Accelerated Weather Tester (product of the Q-Panel Company, Cleveland, Ohio) and exposed to a cycle consisting of 8 hours at 60° C. with light (UV-B) and 4 hours at 50° C. in the dark. Periodically the panels were removed and the total color change ($\Delta E$) and the percent gloss retention were measured with the following results:

| | Hours | $\Delta E$ | % gloss |
|---|-------|------|---------|
| Formulation A: | 500 | 1.3 | 88 |
| | 1000 | 1.5 | 90 |
| | 1500 | 4.2 | 68 |
| | 2000 | 7.2 | 43 |
| | 2500 | (C)* | (C) |
| Formulation B: | 500 | 0.6 | 98 |
| | 1000 | 2.0 | 96 |
| | 1500 | 6.9 | 61 |
| | 2000 | (C) | (C) |

*(C) indicates the appearance of cracking. The test results show that the polymer bound HALS resulting from the use of HALS-peroxide to prepare the resin provides good stabilization. The resin containing polymer bound HALS resisted cracking longer than resin containing a HALS additive of the current art.

EXAMPLE XIII

Preparation of poly(methyl methacrylate)

Methyl n-amyl ketone (300 g) was heated to 120° C. in a jacketed glass reactor equipped with a stirrer, thermometer, reflux condenser and nitrogen gas sparging line. A mixture of 150 g of methyl methacrylate and 8.0 g of HALS peroxide C-I was prepared. A 107 g portion of this mixture was added uniformly at a rate of 26 g per hour to the refluxing solvent over 4 hours. After monomer/initiator addition was completed, the polymerization was continued for two hours at reflux. The poly(methyl methacrylate) was obtained in 92% monomer conversion and had the following molecular weight data by GPC:
$\overline{M}w = 5,580$
$\overline{M}n = 3,100$
$\overline{M}z = 8,400$
$\overline{M}w/\overline{M}n = 1.8$

EXAMPLE XIV

Preparation of polystyrene

The stabilizer-initiator C-IV was used to polymerize styrene monomer using bulk polymerization conditions at 120° C. and 0.28 phm of initiator. The 1:1 complex of this initiator and t-butyl hydroperoxide was also used to polymerize styrene monomer under the same conditions using 0.25 phm of the complex. In each case, the polymerized mass was dissolved in toluene and the polymer precipitated by addition of the toluene solution to a large quantity of rapidly stirred methanol. The polystyrene produced was characterized by the data in Table II for percent conversion, viscosity average molecular weight, and Mn, Mw, and Mz (by GPC).

TABLE II

| Reaction Time (min) | % conversion* | Mv** | Mn | Mw | Mz |
|---|---|---|---|---|---|
| Initiator: OO-t-butyl O-(2,2,6,6-tetramethyl-4-piperidinyl monoperoxycarbonate (C-IV) | | | | | |
| 30 | 36 | 99000 | — | — | — |
| 50 | 56 | 111000 | — | — | — |
| 90 | 89 | 153000 | — | — | — |
| 100 | 99 | 163000 | 89000 | 230000 | 461000 |
| Initiator: OO-t-butyl O-(2,2,6,6-tetramethyl-4-piperidinyl monoperoxycarbonate (C-IV), 1:1 complex with t-butyl hydroperoxide | | | | | |
| 30 | 28 | 104000 | — | — | — |
| 50 | 46 | 117000 | — | — | — |
| 90 | 72 | 139000 | — | — | — |
| 100 | 96 | 166000 | — | — | — |

* - conversion was determined by precipitation of the polymer in methanol.
** - viscosity average molecular weight in toluene at 25° C.

EXAMPLE XV

Preparation of poly(p-methylstyrene)

The stabilizer-initiator C-III was used to prepare a polymer from p-methylstyrene. The polymer was prepared in bulk using 0.28 phm of the initiator and heating the reaction at 120° C. for 150 minutes. The polymerized mass was dissolved in toluene and precipitation of the polymer was done by dropwise addition of the toluene solution to rapidly stirred methanol. The polymer was isolated by filtration. The polymer prepared was analyzed by GPC with the following results:
$\overline{M}w = 469,000$
$\overline{M}n = 105,000$
$\overline{M}z = 1,210,000$
$\overline{M}w/\overline{M}n = 4.5$

EXAMPLE XVI

Preparation and Accelerated Weather Testing of Impact Modified Polystyrene

1. Preparation of impact modified polystyrene A stock solution (A) of 8% polybutadiene (TAKTENE XG 575, from Polysar) in styrene monomer was prepared; and 0.08 part (based on the weight of monomer blend) of initiator was added thereto. A second stock solution (B) of styrene containing 0.53 parts by weight of initiator was prepared. Solution A (62.5 g) was placed in a reaction flask and heated to 100° C. oil bath for about 30 minutes until the solution had become distinctly turbid. The mass was cooled to 50° C. and 37.5 g of solution B was added. The resulting resin mixture was bulk polymerized at 120° C. for 5 hours. The cured polymer was ground using a Brabender Granu-Grinder. The ground polymer was compression molded into about 28–32 mil thick specimens using a Carver hydraulic press (320° F. and approx. 8000 psi for 2 minutes).

2. Accelerated weather test

Accelerated weathering was done in a QUV weathering tester made by Q Panel Company with a 8 hour 60° C. light cycle and a 4 hour 50° C. wet cycle. Samples were removed (in triplicate) at various time intervals and the molecular weight determined using GPC. The results are shown in Table III. The results show that the polymer prepared using the stabilizer initiator of this invention resisted degradation much better than polymer prepared using an initiator with no attached stabilizer.

TABLE III

Accelerated Weathering Test Results Initiator A was HALS peroxide C-1 Initiator B was Lupersol TBEC*

| | | Exposure Time (in hours) | | |
|---|---|---|---|---|
| | | 0 | 500 | 1000 |
| % molecular weight retained using initiator A | $M_n$ | 100 | 68.1 | 67.5 |
| | $M_w$ | 100 | 79.8 | 76.6 |
| | $M_z$ | 100 | 80.1 | 82.0 |
| % molecular weight retained using initiator B | $M_n$ | 100 | 63.3 | 44.6 |
| | $M_w$ | 100 | 73.3 | 62.3 |
| | $M_z$ | 100 | 74.7 | 68.3 |

* - OO-t-butyl O-(2-ethylhexyl) monoperoxycarbonate

What is claimed:

1. A process of preparing a cured polyester containing hindered amine light stabilizer groups chemically connected to the polyester comprising curing an unsaturated polyester resin capable of being cured by free radicals in the presence of a curing amount of a compound having the formula

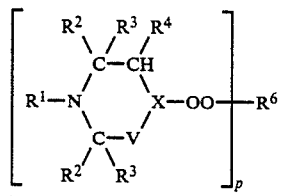

wherein p is 1 or 2, and $R^1$ is selected from hydrogen, substituted or unsubstituted aliphatic of 1–20 carbons, substituted or unsubstituted alicyclic of 5–12 carbons, substituted or unsubstituted araliphatic of 7–22 carbons, substituted or unsubstituted aliphatic acyl of 2–21 carbons, substituted or unsubstituted alicyclic acyl of 6–13 carbons, substituted or unsubstituted aryl acyl of 7–11 carbons, substituted or unsubstituted araliphatic acyl of 7–22 carbons, —C(=O)—N($R^4$)($R^5$), —C(=O)—O—$R^9$, and —(CH$_2$—CH($R^4$)—O)$_r$—$R^4$ where r is 2–50, and $R^2$ and $R^3$ may be the same or different and are independently selected from substituted or unsubstituted aliphatic of 1–20 carbons, substituted or unsubstituted aryl of 6–10 carbons, and substituted or unsubstituted araliphatic of 7–22 carbons, and $R^2$ and $R^3$ can be taken together with the carbon to which they are attached to form a substituted or unsubstituted saturated alicyclic group of 4–12 carbons, and V is selected from —CH($R^5$)— and —C(=O)—, and $R^4$ and $R^5$ may be the same or different and are independently selected from hydrogen, substituted or unsubstituted aliphatic of 1–20 carbons, substituted or unsubstituted aryl of 6–10 carbons, and substituted or unsubstituted araliphatic of 7–22 carbons, substituted or unsubstituted alicyclic of 5–12 carbons which may optionally contain 1–3 heteroatoms selected from oxygen, sulfur, and nitrogen atoms in the ring, the nitrogen atom having a hydrogen atom or a methyl group bonded thereto, with the proviso that multiple heteroatoms must be separated from each other and from the portion of the compound to which the alicyclic group is bonded by at least one carbon atom, and when V is —CH($R^5$)—, X is selected from

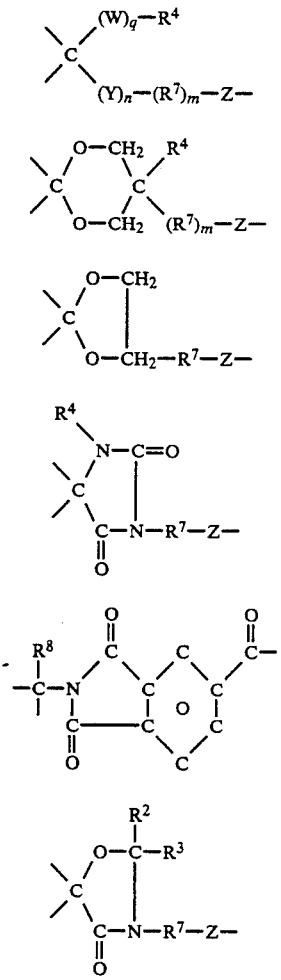

and

-continued

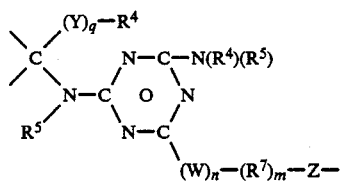

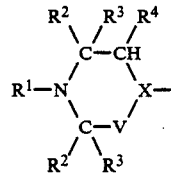

and when V is —C(=O)—, X is $\diagdown$N—R$^7$—Z—, and

R$^7$ is selected from a substituted or unsubstituted aliphatic diradical of 1–20 carbons, substituted or unsubstituted aryl diradical of 6–10 carbons, substituted or unsubstituted alicyclic diradical of 5–12 carbons, and substituted or unsubstituted araliphatic diradical of 7–22 carbons, and the diradical chain(s) may optionally contain 1–6 heteroatoms selected from oxygen, sulfur, and nitrogen atoms, the nitrogen atom having a hydrogen atom or a methyl group bonded thereto, with the proviso that multiple heteroatoms must be separated from each other and from the portion of the compound to which the diradical is bonded by at least one carbon atom, R$^8$ is selected from hydrogen, substituted or unsubstituted aliphatic of 1–20 carbons, substituted or unsubstituted alicyclic of 5–12 carbons, substituted or unsubstituted aryl of 6–10 carbons, substituted or unsubstituted araliphatic of 7–22 carbons, —C(=O)—O—R$^9$, and —(CH$_2$—CH(R$^4$)—O)$_r$—R$^5$, and W is selected from —O—, —S—, and —N(R$^5$)—, and
Y is selected from —Z—, —O—, —S—, —N(R$^4$)—, —S(=O)—, —O—S(=O)—, —O—S(=O)$_2$—, —NH—C(=O)—NH—, —O—C(=O)—O—, —C(=O)—O—, —O—C(=O)—C(=O)—O—, —O—C(=O)—C(=O)—N(R$^4$)—, —N(R$^4$)—C(=O)—C(=O)—O—, and —N(R$^4$)—C(=O)—C(=O)—N(R$^4$)—, n, m and q are integers independently selected from 0 and 1 with the proviso that when m is 0, n must be 0, Z is selected from —C(=O)—, —S(=O)$_2$—, —C(R$^9$)(R$^{10}$)—, —O—C(=O)—, —N(R$^4$)—C(=O)—, —O—C(=O)—C(=O)—, —N(R$^4$)—C(=O)—C(=O)—, —Si(R$^4$)(R$^5$)—, —Si(O—R$^4$)(O—R$^5$)—, and —P(O)(O—R$^4$)(O—R$^5$)—, and when p is 1, R$^6$ is selected from hydrogen, substituted or unsubstituted tertiary aliphatic of 4–24 carbons, substituted or unsubstituted tertiary alicyclic of 6–13 carbons, substituted or unsubstituted tertiary araliphatic of 9–24 carbons, substituted or unsubstituted aliphatic acyl of 2–21 carbons, substituted or unsubstituted aryl acyl of 7–11 carbons, substituted or unsubstituted araliphatic acyl of 8–22 carbons, —C(=O)—N(R$^4$)(R$^5$), —C(=O)—O—R$^9$, —C(R$^9$)(R$^{10}$)—C(=O)—O—R$^4$, —S(=O)$_2$—R$^4$, and when p is 2, R$^6$ is selected from substituted or unsubstituted di-tertiary aliphatic of 6–27 carbons, substituted or unsubstituted di-tertiary alicyclic diradical of 7–14 carbons, substituted or unsubstituted di-tertiary araliphatic of 12–27 carbons, substituted or unsubstituted aliphatic diacyl of 3–21 carbons, substituted or unsubstituted alicyclic diacyl of 7–15 carbons, substituted or unsubstituted aryl diacyl of 8–12 carbons, or substituted or unsubstituted araliphatic diacyl of 9–24 carbons, R$^9$ and R$^{10}$ are independently selected from substituted or unsubstituted aliphatic of 1–20 carbons, substituted or unsubstituted aryl of 6–10 carbons, substituted or unsubstituted araliphatic of 7–22 carbons, and substituted or unsubstituted alicyclic of 5–12 carbons which may optionally contain 1–3 heteroatoms selected from oxygen, sulfur, and nitrogen atoms in the ring, the nitrogen atom having a hydrogen atom or a methyl group bonded thereto, with the proviso that multiple heteroatoms must be separated from each other and from the portion of the compound to which the alicyclic group is bonded by at least one carbon atoms, and when both are present, R$^9$ and R$^{10}$ can be connected to each other by an alkylene diradical bridge containing 4–9 carbons, which may optionally contain 1–3 heteroatoms selected from oxygen, sulfur, and nitrogen atoms in the ring, the nitrogen atom having a hydrogen atom or a methyl group bonded thereto, with the provisos that multiple heteroatoms must be separated from each other and from the portions of the compound to which the diradical bridge is bonded by at least one carbon atom, and when R$^6$ is tertiary aliphatic, tertiary alicyclic or tertiary araliphatic, R$^{10}$ may also be selected from —OO—R$^6$ and —O—R$^9$, and optional substituents for R$^1$, R$^2$, R$^3$, R$^4$, R$^5$, R$^6$, R$^7$, R$^8$, R$^9$ and R$^{10}$ are one or more groups selected from halogen, alkyl of 1–8 carbons, alkoxy of 1–8 carbons, —C≡N, —OH, epoxy, carboxy, alkoxycarbonyl of 2–6 carbons, acyloxy of 1–4 carbons, acryloyl, acryloyloxy, methacryloyl, methacryloyloxy, hydroxymethyl, hydroxyethyl, alkylmercapto of 1–4 carbons and trialkoxysilyl of 3–12 carbons.

2. The process of claim 1 wherein R$^1$ is selected from hydrogen, substituted or unsubstituted alkyl of 1–4 carbons, allyl, 2-hydroxyethyl, 2,3-epoxypropyl, 2-acetoxyethyl, benzyl, alkanoyl of 2–5 carbons, cyclohexylcarbonyl, benzoyl or phenacyl, R$^2$ and R$^3$ may be the same or different and are independently selected from alkyl of 1–4 carbons, benzyl or taken together with the carbon to which they are attached to form a cyclohexane ring, R$^4$ and R$^5$ may be the same or different and are independently selected from hydrogen, alkyl of 1–8 carbons, phenyl, benzyl, cycloalkyl of 5–7 carbons or 2,2,6,6-tetramethyl-4-piperidinyl, and X is selected from

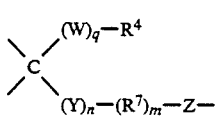 and 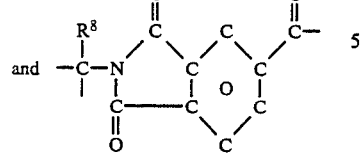

and

R⁷ is selected from alkylene of 1-10 carbons, arylene of 6-10 carbons, aralkylene of 8-16 carbons or cycloalkylene of 4-8 carbons, R⁸ is selected from hydrogen, alkyl of 1-8 carbons, phenyl, benzyl, cycloalkyl of 5-7 carbons or 2,2,6,6-tetramethyl-4-piperidinyl, Y is selected from —O—, —S—, —N(R⁹)—, —O—(—=O)—O—, —C(=O)—O—, and Z, Z is selected from —C(=O)—, —C(R⁹)(R¹⁰)—, and —O—C(=O)—, and when p is 1, R⁶ is selected from t-alkyl of 4-10 carbons, t-aralkyl of 9-12 carbons, acyl of 2-10 carbons and aroyl of 7-11 carbons,

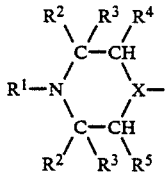

and when p is 2, R⁶ is selected from di-tertiary alkylene of 6-12 carbons, ditertiary aralkylene of 12-15 carbons, alkanedioyl of 3-6 carbons and aryl diacyl of 8-12 carbons, R⁹ and R¹⁰ are independently selected from alkyl of 1-8 carbons, phenyl, benzyl, cycloalkyl of 5-7 carbons or 2,2,6,6-tetramethyl-4-piperidinyl, and may be connected to each other by an alkylene diradical bridge containing 4-9 carbons, and when R⁶ is t-alkyl, t-cycloalkyl, or t-aralkyl, R¹⁰ may also be selected from —OO—R⁶, and optional substituents for R², R², R³, R⁴, R⁵, R⁶, R⁷, R⁸, R⁹ and R¹⁰ are one or more groups selected from —Cl, —Br, alkyl of 1-4 carbons, alkoxy or 1-8 carbons, —C≡N, —OH, epoxy, carboxy, alkyoxycarbonyl of 2-6 carbons, and acyloxy of 1-4 carbons.

3. The process of claim 2 wherein
p is 1, and
q is 0, and
R¹ is selected from hydrogen, substituted or unsubstituted alkyl of 1-4 carbons, 2-hydroxyethyl, 2-acetoxyethyl, and alkanoyl of 2-5 carbons,
R² and R³ may be the same or different and are independently selected from alkyl of 1-4 carbons,
R⁴ and R⁵ may be the same or different and are independently selected from hydrogen, alkyl of 1-8 carbons,
R⁷ is selected from alkylene of 1-10 carbons and aralkylene of 8-16 carbons,
R⁸ is selected from hydrogen, alkyl of 1-8 carbons, phenyl and benzyl, and
when p is 1, R⁶ is selected from t-alkyl of 4-10 carbons, t-aralkyl of 9-12 carbons, acyl of 2-10 carbons, aroyl of 7-11 carbons, and and R⁹ and R¹⁰ are independently selected from alkyl of 1-8 carbons and phenyl, and optional substituents for R¹, R², R³, R⁴, R⁵, R⁶, R⁷, R⁸, R⁹ and R¹⁰ are one or more groups selected from alkoxy of 1-8 carbons, —OH, carboxy, alkyoxycarbonyl of 2-6 carbons, and acyloxy of 1-4 carbons.

4. The process of claim 3 in which R¹, R², and R³ are methyl, R⁴ and R⁵ are hydrogen, X is

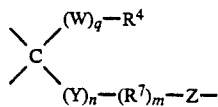

n, m, and q are 0, Z is —O—C(=O)—, and R⁶ is t-butyl or t-amyl.

5. The process of claim 3 in which R¹, R² and R³ are methyl, R⁴ and R⁵ are hydrogen, X is

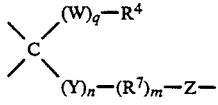

n and m are 1, q is 0, Y is —O—(=O)—O—, R⁷ is —CH(CH₃)—CH₂—, Z is —C(R⁹)(R¹⁰), R⁹ and R¹⁰ are methyl, and R⁶ is t-butyl.

6. The process of claim 3 in which R¹ is hydrogen or acetyl, R² and R³ are methyl, R⁴ and R⁵ are hydrogen, X is

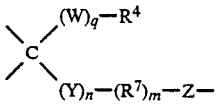

n, m, and q are 0, Z is —O—C(=O)—, and R⁶ is t-butyl.

7. The process of claim 3 in which R¹, R² and R³ are methyl, R⁴ and R⁵ are hydrogen, X is

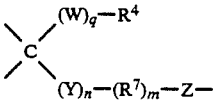

n and m are 1, q is 0, Y is —O—C(=O)— or —NH—C(=O)—, R⁷ is —CH₂—CH₂—, Z is —C(=O)—, and R⁶ is t-butyl.

8. The process of claim 3 in which R¹ is 2-acetoxyethyl, R² and R³ are methyl, R⁴ and R⁵ are hydrogen, X is

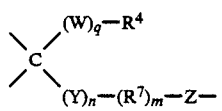
n and m are 1, q is 0, Y is —O—C(=O)—O—, $R^7$ is —CH(CH$_3$)—CH$_2$, Z is —C($R^9$)($R^{10}$)—, $R^9$ and $R^{10}$ are methyl, $R^6$ is t-butyl.
9. The process of claim 3 in which $R^1$ is hydrogen, $R^2$ and $R^3$ are methyl, $R^4$ and $R^5$ are hydrogen, X is
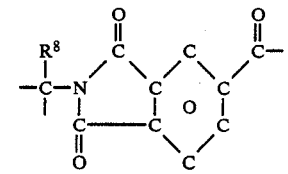
and $R^8$ is hydrogen, and $R^6$ is t-amyl.
10. The stabilized cured polyester prepared by the process of any one of claims 1 through 9.
* * * * *

UNITED STATES PATENT AND TRADEMARK OFFICE
CERTIFICATE OF CORRECTION

PATENT NO. : 4,885,347
DATED : December 5, 1989
INVENTOR(S) : Terry N. Myers

It is certified that error appears in the above-identified patent and that said Letters Patent is hereby corrected as shown below:

In the claims:

In claim 1, at column 26, line 32, change "atoms" to ---atom--.

In claim 2, at column 27, lines 18 and 19, change "-O-(=O)-O-" to -- -O-C(=O)-O- --;

line 47, change "or" to --of--.

In claim 5, at column 28, line 39, change "-O-(=O)-O-" to -- -O-C(=O)-O- --.

Signed and Sealed this

Eighteenth Day of December, 1990

Attest:

HARRY F. MANBECK, JR.

*Attesting Officer*  *Commissioner of Patents and Trademarks*